(12) United States Patent
Hamada et al.

(10) Patent No.: US 7,022,422 B2
(45) Date of Patent: Apr. 4, 2006

(54) LUMINESCENT MATERIAL FOR LIGHT EMITTING DEVICE AND ORGANIC ELECTROLUMINESCENT DEVICE

(75) Inventors: Yuji Hamada, Nara (JP); Noriyuki Matsusue, Hirakata (JP); Kazuki Nishimura, Hirakata (JP)

(73) Assignee: Sanyo Electric Co. Ltd., Moriquchi (JP)

( * ) Notice: Subject to any disclaimer, the term of this patent is extended or adjusted under 35 U.S.C. 154(b) by 0 days.

(21) Appl. No.: 10/376,099

(22) Filed: Feb. 26, 2003

(65) Prior Publication Data

US 2003/0194580 A1    Oct. 16, 2003

(30) Foreign Application Priority Data

Feb. 27, 2002   (JP)   .............................. 2002-051802

(51) Int. Cl.
  *H05B 33/14*   (2006.01)
  *C09K 11/06*   (2006.01)
(52) U.S. Cl. ...................... 428/690; 428/917; 313/504; 257/102; 257/E51.044; 546/4; 546/10; 556/32; 556/35; 556/137
(58) Field of Classification Search ............... 428/690, 428/917; 313/504; 257/40, 102, 103; 252/301.16; 546/2, 4, 10; 556/32, 33, 35, 137
See application file for complete search history.

(56) References Cited

U.S. PATENT DOCUMENTS

2002/0034656 A1 *  3/2002  Thompson et al. .......... 428/690
2002/0100906 A1 *  8/2002  Takiguchi et al. ............ 257/40
2003/0108769 A1 *  6/2003  Heuer et al. ................. 428/690

OTHER PUBLICATIONS

K. Dedeian et al., "A New Synthetic Route to the Preparation of a Series of Strong Photoreducing Agents fac Tris-Ortho-Metalated Complexes of Iridium (III) with Substituted 2-Phenylpyridines", Inorg. Chem. 1991, 30, pp. 1685 to 1687.
S. Lamansky et al., "Highly Phosphorescent Bis-Cyclometalated Iridium Complexes: Synthesis, Photophysical Characterization, and Use in Organic Light Emitting Diodes", J. Am. Chem. Soc. 2001, 123, pp. 4304 to 4312 (published on Web Apr. 13, 2001.).

* cited by examiner

Primary Examiner—Marie Yamnitzky
(74) Attorney, Agent, or Firm—W. F. Fasse; W. G. Fasse

(57) ABSTRACT

A luminescent material for a light emitting device represented by the following general formula (1) or (2)

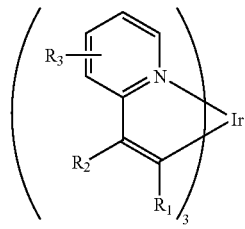

(1)

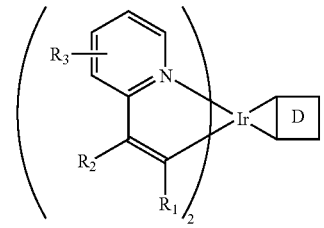

(2)

or represented by any of general formulae (3) to (16) as described herein,
wherein D is a ligand represented by the following general formula (17) or (18)

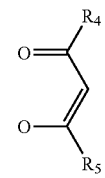

(17)

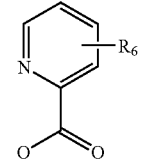

(18)

and $R_1$ through $R_6$ are as described herein.

17 Claims, No Drawings

LUMINESCENT MATERIAL FOR LIGHT EMITTING DEVICE AND ORGANIC ELECTROLUMINESCENT DEVICE

BACKGROUND OF THE INVENTION

1. Field of the Invention

The present invention relates to a luminescent material used for light emitting devices such as organic electroluminescent (EL) devices and electrochemiluminescent (ECL) devices.

2. Related Art

In recent years, semiconductor circuits have had greater density, and hence miniaturization and portability of sophisticated information terminals are enabled. In such circumstances, researches on a display device of low-profile, light weight and low power consumption are actively conducted. For example, a liquid crystal display (LCD) is widely applied to displays of small-sized portable devices and notebook computers, and have developed such that it is even replacement to a cathode ray tube (CRT) display. In addition, as a display device of next generation type that can support moving pictures, organic EL devices attract attention.

An electrochemiluminescent (ECL) device is also one of such type of devices. Likewise the organic EL device, an ECL device is also a self-luminescent device, and the primary characteristic of the ECL device is that the light emission is obtained from a solution.

As a luminescent material used for the above-mentioned light emitting device such as organic EL device, those exhibiting high brightness in response to applied voltage and current, or those having high luminous efficiency are requested. As such a luminescent material, materials which emit light from the triplet state, such as Tris (2-phenylpyridine) iridium: Ir(ppy)$_3$ and the like, are known.

SUMMARY OF THE INVENTION

It is an object of the present invention to provide a novel luminescent material for light emitting device having high luminous efficiency and a light emitting device using the same.

Luminescent materials for light emitting device according to the present invention are iridium-containing organic metal compounds represented by the following general formulae (1) to (16) as follows:

(1)

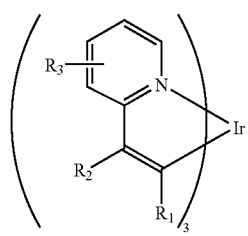

(2)

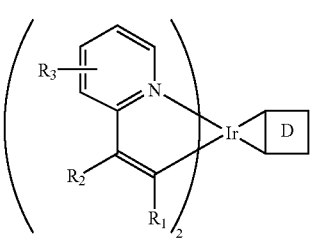

(3)

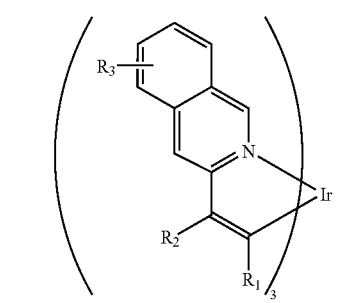

(4)

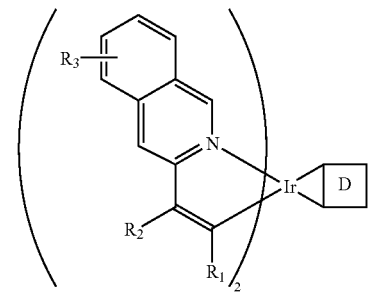

(5)

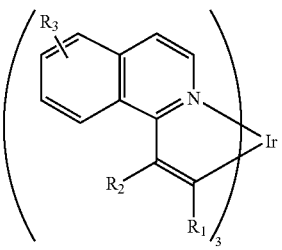

(6)

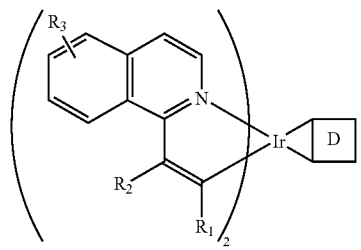

(7)

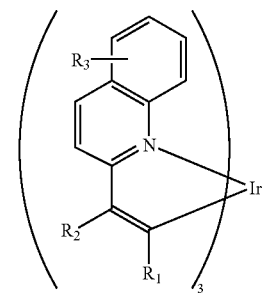

(8) 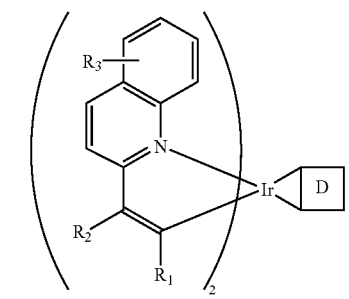

(9) 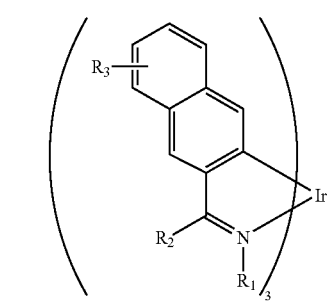

(10) 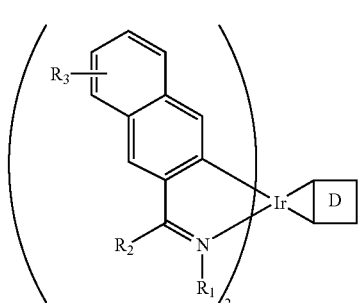

(11) 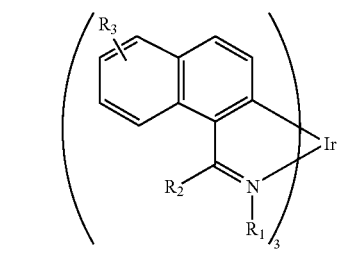

(12) 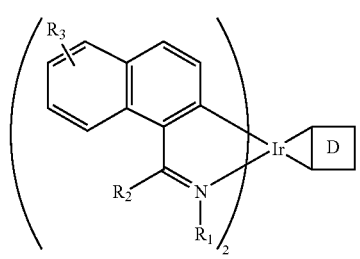

(13) 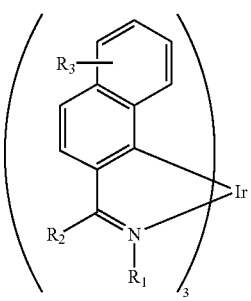

(14) 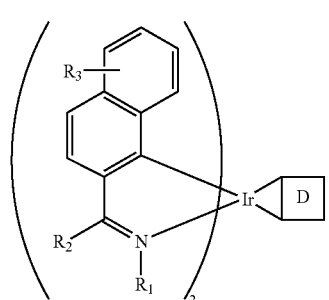

(15) 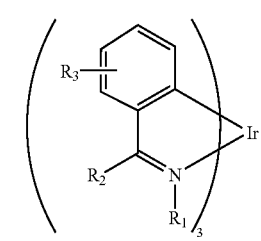

(16) 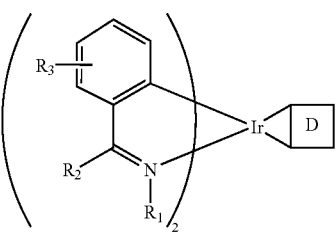

wherein $R_1$, $R_2$ and $R_3$ are H, $C_nH_{2n+1}$ (n is preferably an integer of 1 to 10, more preferably an integer of 1 to 5), $N(C_nH_{2n+1})_2$ (n is preferably an integer of 1 to 10, more preferably an integer of 1 to 5), $COOC_nH_{2n+1}$ (n is preferably an integer of 1 to 10, more preferably an integer of 1 to 5), F, Cl, Br, I, CN, an optionally substituted phenyl group, an optionally substituted naphthyl group or a phenyl methyl group, which may be the same or different from each other. At least one of $R_1$ and $R_2$ may be $N(C_nH_{2n+1})_2$ (n is an integer of 1 to 10), F, Cl, Br, I, CN, an optionally substituted phenyl group, an optionally substituted naphthyl group or a phenyl methyl group. D is a ligand represented by the following general formula (17) or (18).

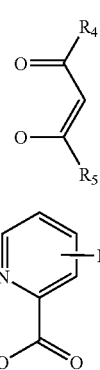

(17)

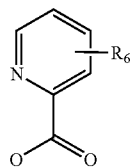

(18)

Therein $R_4$, $R_5$ and $R_6$ are H, $C_nH_{2n+1}$ (n is preferably an integer of 1 to 10, more preferably an integer of 1 to 5), $N(C_nH_{2n+1})_2$ (n is preferably an integer of 1 to 10, more preferably an interger of 1 to 5), $COOC_nH_{2n+1}$ (n is preferably an integer of 1 to 10, more preferably an interger of 1 to 5), F, Cl, Br, I, CN, $CF_3$, a furyl group, a thienyl group, an optionally subdtituted phenyl group or an optionally substituted naphthyl group, which may be the same or different from each other.

The luminescent materials of the present invention are materials which emit light from the triplet state, and hence have high luminous efficiency.

The luminescent materials represented by the general formulae (1), (3), (5), (7), (9), (11), (13) and (15) can be synthesized by a method described in "Inorg Chem. 1991, 30, pp.1685 to 1687." To be more specific, they can be systhesized by allowing iridium acetylacetonato ($Ir(acac)_3$) to react with a nitrogen containing compound which is to be a ligand.

The luminescent material represented by the general formulae (2), (4), (6), (8), (10), (12), (14) and (16) can be synthesized by the method described in "J. Am. Chem. Soc. 2001, 123, pp. 4304 to 4312." More specifically, the synthesis can be achieved by causing a nitrogen containing compound which is to be a ligand to react with an iridium cholorate to synthesize a dimer bridged by chorine, and then causing this dimer to react with a ligand D.

The luminescent material of the present invention can be used as a luminescent material for organic EL devices and ECL devices and the like. When used as a luminescent material for organic EL device, it may be used as a dopant which is contained in a luminescent layer together with a host. The content when used as a dopant is preferably 0.5% by weight or more, and more preferably in the range of 0.5 to 30% by weight, but not particularly limited thereto.

An organic EL device of the present invention is characterized by containing the above-mentioned luminescent material of the present invention in a luminescent layer.

DESCRIPTION OF THE PREFERRED EMBODIMENTS

The present invention will now be described by way of specific examples, however, it is to be noted that the present invention is not limited to the following examples.

EXAMPLES 1 TO 14

An anode made of ITO was formed on a glass substrate, and a hole transfer layer, a luminescent layer, a hole preventive layer, an electron transfer layer and a cathode were formed thereon by vacuum deposition, to thereby produce an organic EL device having a device structure of anode/hole transfer layer/luminescent layer/hole preventive layer/electron transfer layer/cathode.

As the anode, an ITO film having a film thickness of 1000 Å was formed. As the hole transfer layer, an NPB layer having a thickness of 500 Å was formed. As the luminescent layer, a layer of CBP serving as a host to which 6.5% by weight of dopant was added was formed so as to have a thickness of 100 Å. As the hole preventive layer, a BCP layer having a thickness of 100 Å was formed. As the electron transfer layer, an Alq layer having a thickness of 300 Å was formed. As the cathode, a MgIn layer having a thickness of 2000 Å was formed.

As the dopant to be contained in the luminescent layer, Compounds 1 to 14 which are the luminescent materials of the present invention and represented by the following general formulae were used.

COMPOUND 1

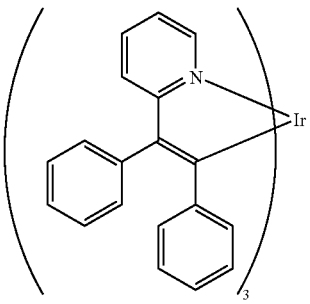

Compound 1 has the structure as follows:

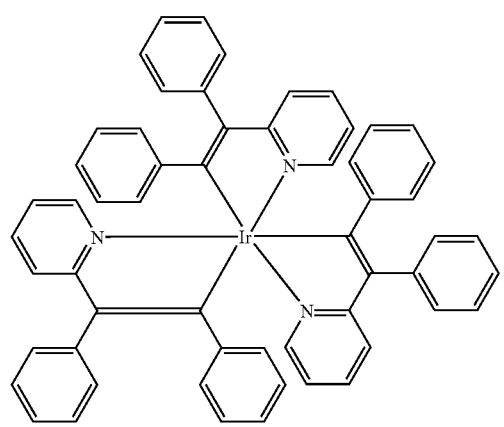

COMPOUND 2

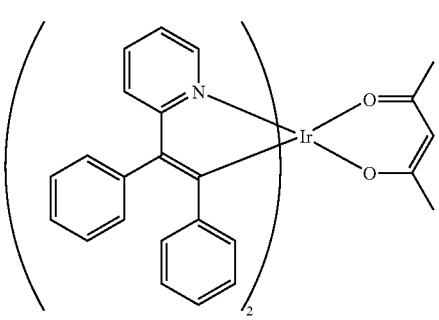

COMPOUND 3
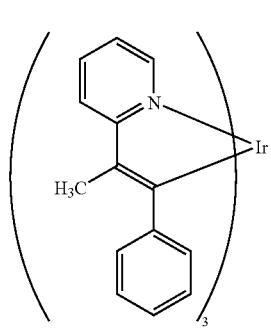
COMPOUND 8
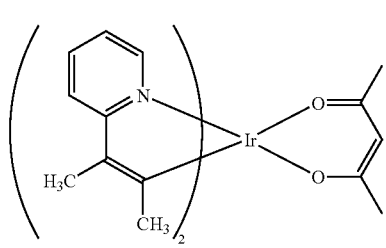
COMPOUND 4
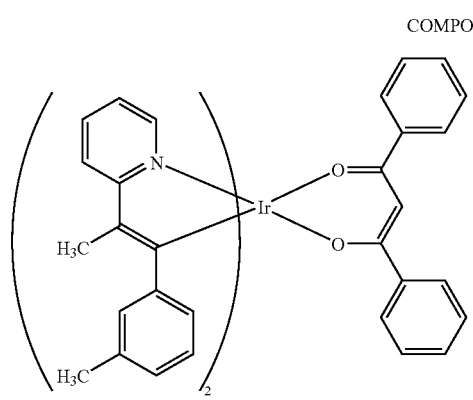
COMPOUND 9
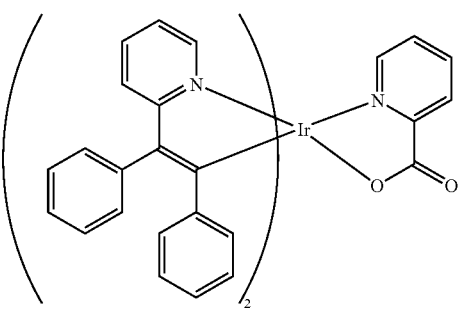
COMPOUND 5
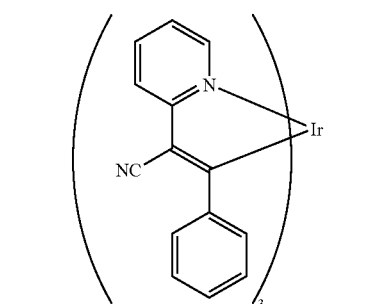
COMPOUND 10
COMPOUND 6
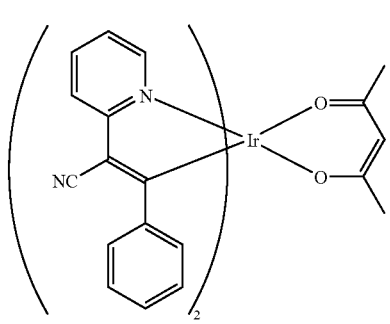
COMPOUND 11
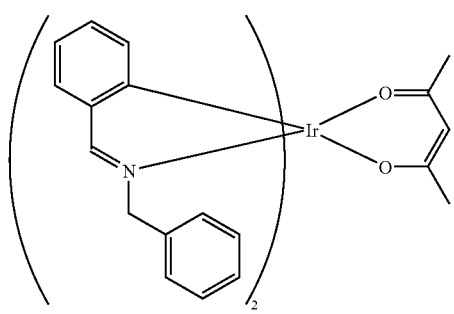
COMPOUND 7
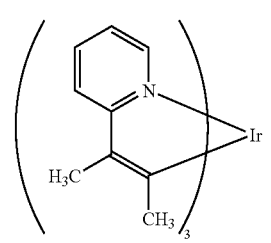

-continued

COMPOUND 12

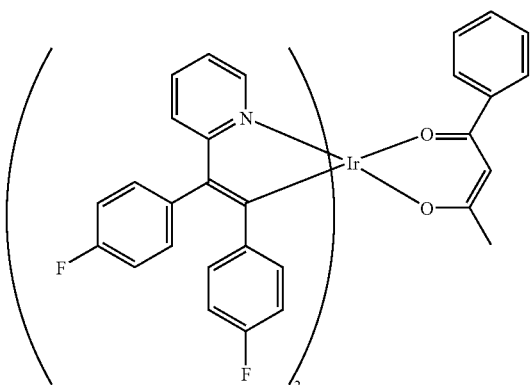

COMPOUND 13

COMPOUND 14

NPB used for the hole transfer layer is N,N'-di(naphthalene-1-yl)-N,N'-diphenyl-benzidine and is a compound having the following structure.

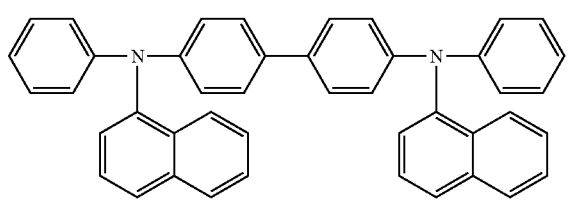

NPB

CBP used for the host of the luminescent layer is 4,4'-bis(carbazole-9-yl)-biphenyl and is a compound having the following structure.

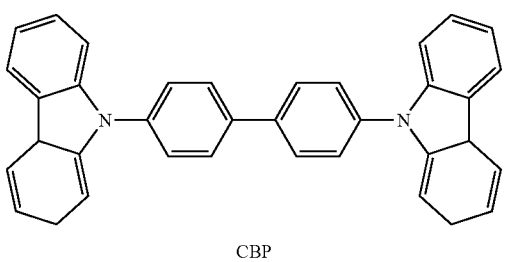

CBP

BCP used for the hole preventive layer is 2,9-dimethyl-4,7-diphenyl-1,10-phenanthroline and is a compound having the following structure.

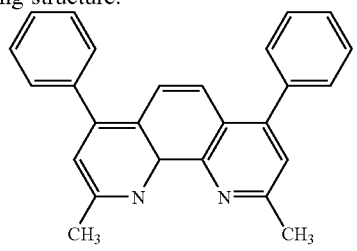

BCP

Alq used for the electron transfer layer is Tris(8-hydroxyquinolinato) aluminum, and is a compound having the following structure.

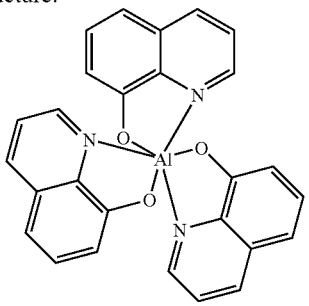

Alq

COMPARATIVE EXAMPLE 1

An organic EL device was produced in the same manner as the above-mentioned examples except that as the dopant contained in the luminescent layer, 2,3,7,8,12,13,17,18-octaethyl-21H,23H-porphyrin platinum (II) (PtOEP) which is a conventional luminescent material having the following structure was used.

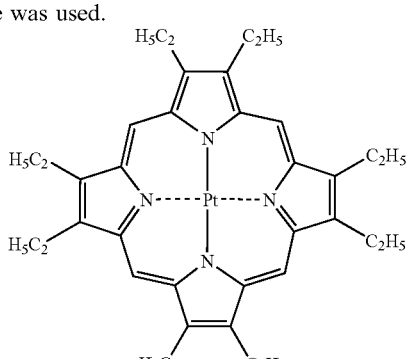

PtOEP

[Evaluation of Luminous Characteristics of Organic EL Devices]

With respect to the organic EL devices of Examples 1 to 14 and Comparative example 1 produced in the manner as described above, a current of 10 mA/cm² was applied to electrodes, and maximum brightness, luminous efficiency, emission wavelength and chromaticity coordinates were measured. Results of measurement are shown in Table 1. Herein the concentration of the dopant indicated in Table 1 is 6.5% by weight.

TABLE 1

| | Luminescent Layer | | Maximum Brightness (cd/m²) | Luminous Efficiency (cd/A) | Emission Wavelength (nm) | Chromaticity Coordinates (x, y) |
|---|---|---|---|---|---|---|
| | Host | Dopant (Concentration) | | | | |
| Ex. 1 | CBP | Compound 1 (6.5%) | 21,000 | 10.2 | 607 | 0.58, 0.42 |
| Ex. 2 | CBP | Compound 2 (6.5%) | 22,000 | 11 | 606 | 0.58, 0.42 |
| Ex. 3 | CBP | Compound 3 (6.5%) | 23,000 | 12 | 575 | 0.51, 0.47 |
| Ex. 4 | CBP | Compound 4 (6.5%) | 23,100 | 12 | 574 | 0.50, 0.47 |
| Ex. 5 | CBP | Compound 5 (6.5%) | 16,900 | 9.4 | 630 | 0.63, 0.36 |
| Ex. 6 | CBP | Compound 6 (6.5%) | 15,900 | 9.3 | 629 | 0.63, 0.36 |
| Ex. 7 | CBP | Compound 7 (6.5%) | 21,200 | 10.8 | 545 | 0.42, 0.47 |
| Ex. 8 | CBP | Compound 8 (6.5%) | 22,000 | 11.1 | 543 | 0.42, 047 |
| Ex. 9 | CBP | Compound 9 (6.5%) | 12,000 | 8 | 648 | 0.66, 0.33 |
| Ex. 10 | CBP | Compound 10 (6.5%) | 17,600 | 9.6 | 605 | 0.58, 0.42 |
| Ex. 11 | CBP | Compound 11 (6.5%) | 15,000 | 9.2 | 492 | 0.19, 0.28 |
| Ex. 12 | CBP | Compound 12 (6.5%) | 24,000 | 10.8 | 589 | 0.56, 0.43 |
| Ex. 13 | CBP | Compound 13 (6.5%) | 15,800 | 9.2 | 628 | 0.63, 0.36 |
| Ex. 14 | CBP | Compound 14 (6.5%) | 15,300 | 9.1 | 603 | 0.58, 0.42 |
| Comp. Ex. 1 | CBP | PtOEP (8%) | 1,200 | 0.8 | 657 | 0.68, 0.31 |

As is apparent from Table 1, Examples 1 to 14 using the luminescent materials of the present invention are superior in luminous efficiency to Comparative example 1 using the conventional luminescent material. The luminescent materials of the present invention are considered as materials which emit light from the triplet state since they are iridium-containing organic metal compounds and have high luminous efficiency.

EXAMPLES 15 TO 18

Organic EL devices were produced in the same manner as Example 1 except that the concentrations of Compound 1 to be contained in the luminescent layer as the dopant were 0.5% by weight, 3% by weight, 15% by weight and 30% by weight, respectively.

With respect to the organic EL devices thus produced, maximum brightness, luminous efficiency, emission wavelength and chromaticity coordinates were measured. Results of measurement are shown in Table 2. Table 2 also shows the result for Example 1.

TABLE 2

| | Luminescent Layer | | Maximum Brightness (cd/m²) | Luminous Efficiency (cd/A) | Emission Wavelength (nm) | Chromaticity Coordinates (x, y) |
|---|---|---|---|---|---|---|
| | Host | Dopant (Concentration) | | | | |
| Ex. 1 | CBP | Compound 1 (6.5%) | 21,000 | 10.2 | 607 | 0.58, 0.42 |
| Ex. 15 | CBP | Compound 1 (0.5%) | 8,500 | 10.7 | 595 | 0.55, 0.45 |
| Ex. 16 | CBP | Compound 1 (3%) | 21,500 | 10.7 | 602 | 0.57, 0.43 |
| Ex. 17 | CBP | Compound 1 (15%) | 17,000 | 9.6 | 630 | 0.65, 0.35 |
| Ex. 18 | CBP | Compound 1 (30%) | 13,500 | 10.7 | 630 | 0.65, 0.35 |

As is apparent from Table 2, high luminous efficiency is achieved when the content of the dopant in the luminescent layer is in the range of 0.5% by weight to 30% by weight.

EXAMPLES 19 TO 21

Organic EL devices were produced in the same manner as in Example 1 except that TCPB, TCTA and 1AZM-Hex were used as the host to be contained in the luminescent layer.

TCPB is 1,3,5-Tris(carbazole-9-yl)-benzene and is a compound having the following structure.

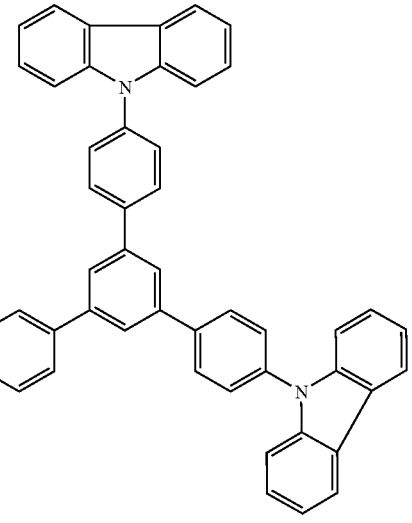

TCPB

TCTA is 4,4', 4"-Tris (carbazole-9-yl)-triphenylamine and is a compound having the following structure.

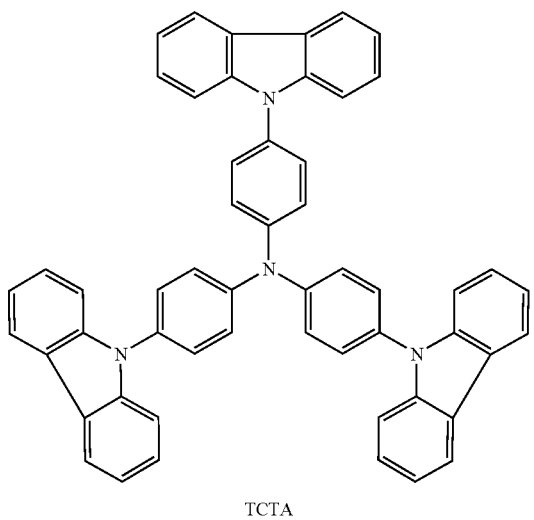

TCTA

1AZM-Hex is (N,N'-disalicylidene-1,6-hexanediaminato) zinc (II) and is a compound having the following structure.

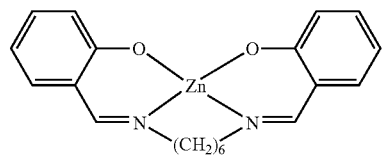

1AZM-Hex

With respect to the organic EL devices thus produced, maximum brightness, luminous efficiency, emission wavelength and chromaticity coordinates were measured. Results of measurement are shown in Table 3.

EXAMPLES 22 AND 23

In Example 22, an organic EL device was produced in the same manner as Example 1 except that for the hole preventive layer, BAlq was used in place of BCP.

BAlq is bis-(2-methyl-8-quinolinolato)-4-(phenyl-phenolato) aluminum (III) and is a compound having the following structure.

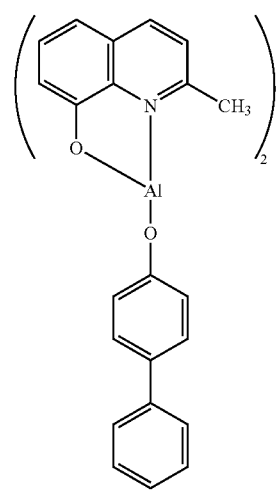

BAlq

In Example 23, an organic EL device was produced in the same manner as Example 1 except that as the cathode material, a cathode having a two-layer structure of LiF/Al was used in place of MgIn.

With respect to the organic EL devices thus produced, maximum brightness, luminous efficiency, emission wavelength and chromaticity coordinates were measured. Results of measurement are shown in Table 4.

TABLE 3

|  | Luminescent Layer | | Maximum | Luminous | Emission | Chromaticity |
|---|---|---|---|---|---|---|
|  | Host | Dopant (Concentration) | Brightness (cd/m²) | Efficiency (cd/A) | Wavelength (nm) | Coordinates (x, y) |
| Ex. 19 | TCPB | Compound 1 (6.5%) | 22,000 | 10.3 | 630 | 0.65, 0.35 |
| Ex. 20 | TCTA | Compound 1 (6.5%) | 20,000 | 9.9 | 630 | 0.65, 0.35 |
| Ex. 21 | 1AZM-Hex | Compound 1 (6.5%) | 21,000 | 10 | 630 | 0.65, 0.35 |

As is apparent from Table 3, even when the host to be contained in the luminescent layer was changed, high luminous efficiency is obtained.

TABLE 4

|  | Luminescent Layer | | Hole Preventive Layer | Electron Transfer Layer | Cathode | Maximum Brightness (cd/m²) | Luminous Efficiency (cd/A) | Emission Wavelength (nm) | Chromaticity Coordinates (x, y) |
|---|---|---|---|---|---|---|---|---|---|
|  | Host | Dopant (Concentration) | | | | | | | |
| Ex. 22 | CBP | Compound 2(6.5%) | BAlq | Alq | MgIn | 23,500 | 11 | 602 | 0.57, 0.43 |
| Ex. 23 | CBP | Compound 1(6.5%) | BCP | Alq | LiF/Al | 35,000 | 15 | 602 | 0.57, 0.43 |

As is apparent from Table 4, high luminous efficiency is obtained in both of the cases that BAlq is used as the material for the hole preventive layer and that LiF/Al is used as the cathode material.

By using the luminescent materials of the present invention, it is possible to improve the luminous efficiency in light emitting devices such as organic EL devices and ECL devices. Therefore, the luminescent materials of the present invention are useful for light emitting devices in appliances that are driven at low voltages such as portable devices.

What is claimed is:

1. A luminescent material for a light emitting device represented by any one of the following general formulae 3 to 14:

formula 3:

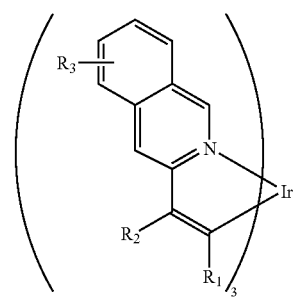

formula 4:

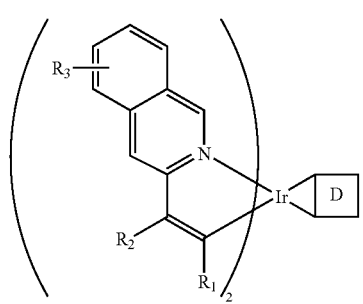

formula 5:

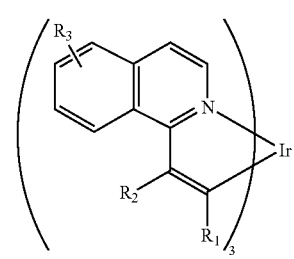

formula 6:

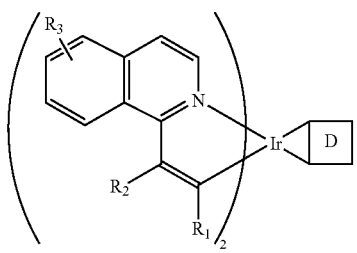

formula 7:

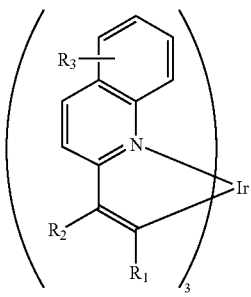

formula 8:

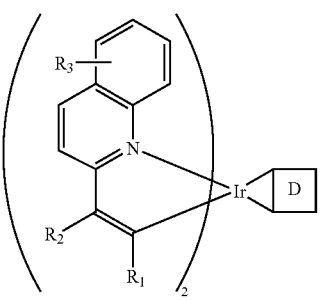

formula 9:

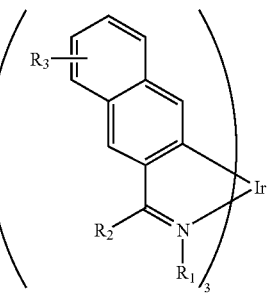

formula 10:

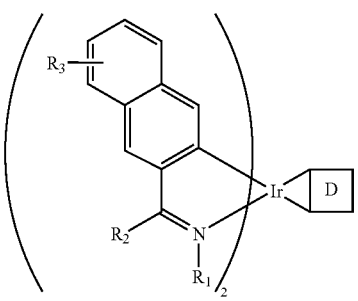

formula 11:

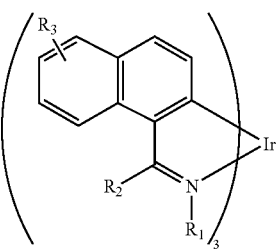

formula 12:

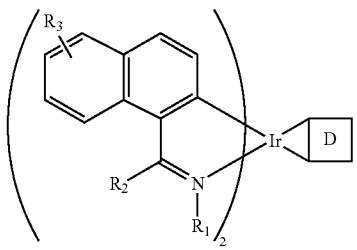

formula 13:

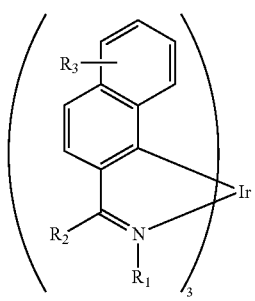

formula 14:

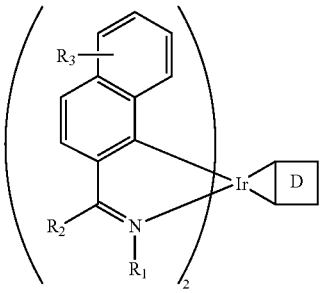

wherein $R_1$, $R_2$ and $R_3$ are H, $C_nH_{2n+1}$ (n is an integer of 1 to 10), $N(C_nH_{2n+1})_2$ (n is an integer of 1 to 10), $COOC_nH_{2n+1}$ (n is an integer of 1 to 10), F, Cl, Br, I, CN, an optionally substituted plenyl group, an optionally substituted naphthyl group or a phenyl methyl group, which may be the same or different from each other, provided that at least one of $R_1$ and $R_2$ is $N(C_nH_{2n+1})_2$ (n is an integer of 1 to 10), F, Cl, Br, I, CN, an optionally substituted phenyl group, an optionally substituted naphthyl group or a phenyl methyl group; and D is a ligand represented by the following general formulae 17 or 18:

formula 17:

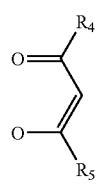

formula 18:

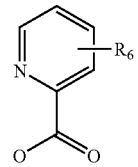

wherein $R_4$, $R_5$ and $R_6$ are H, $C_nH_{2n+1}$ (n is an integer of 1 to 10), $N(C_nH_{2n+1})_2$ (n is an integer of 1 to 10), $COOC_nH_{2n+1}$ (n is an integer of 1 to 10), F, Cl, Br, I, CN, $CF_3$, a furyl group, a thienyl group, an optionally substituted phenyl group or an optionally substituted naphthyl group, which may he the same or different from each other.

2. An organic electroluminescent device comprising a luminescent layer containing the luminescent material according to claim 1.

3. The organic electroluminescent device according to claim 2, wherein said luminescent material is contained as a dopant in said luminescent layer.

4. The luminescent material according to claim 1, represented by said formula 3.

5. The luminescent material according to claim 1, represented by said formula 4.

6. The luminescent material according to claim 1, represented by said formula 5.

7. The luminescent material according to claim 1, represented by said formula 6.

8. The luminescent material according to claim 1, represented by said formula 7.

9. The luminescent material according to claim 1, represented by said formula 8.

10. The luminescent material according to claim 1, represented by said formula 9.

11. The luminescent material according to claim 1, represented by said formula 10.

12. The luminescent material according to claim 1, represented by said formula 11.

13. The luminescent material according to claim 1, represented by said formula 12.

14. The luminescent material according to claim 1, represented by said formula 13.

15. The luminescent material according to claim 1, represented by said formula 14.

16. The luminescent material according to claim 1, wherein at least one of $R_1$ and $R_2$ is F, Cl, Br, I or CN.

17. The luminescent material according to claim 1, wherein at least one of $R_1$ and $R_2$ is $N(C_nH_{2n+1})_2$ (n is an integer of 1 to 10).

* * * * *

UNITED STATES PATENT AND TRADEMARK OFFICE
CERTIFICATE OF CORRECTION

PATENT NO.        : 7,022,422 B2
APPLICATION NO. : 10/376099
DATED             : April 4, 2006
INVENTOR(S)       : Hamada et al.

It is certified that error appears in the above-identified patent and that said Letters Patent is hereby corrected as shown below:

Title page,
Item [75], Inventors,
Line 1, replace "Nara" by --Ikoma-gun—;
Item [73], Assignee,
Line 1, replace "Moriquchi" by --Moriguchi--;

Column 5,
Line 18, replace "Therein" by --Therein,--;
Line 24, after "optionally", replace "subdtituted" by --substituted--.

Column 12,
Lines 33 to 53, replace the chemical structure diagram labeled "TCPB" with:

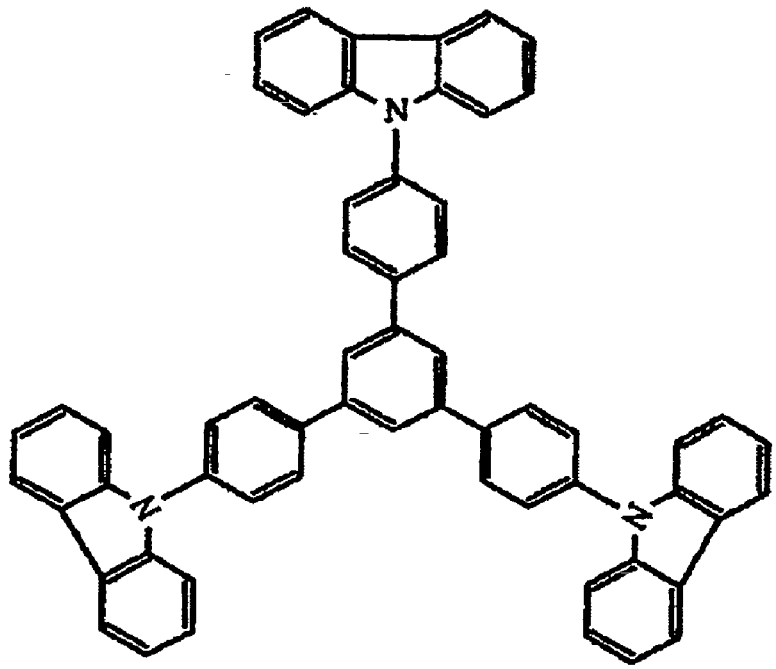

TCPB

UNITED STATES PATENT AND TRADEMARK OFFICE
CERTIFICATE OF CORRECTION

PATENT NO. : 7,022,422 B2
APPLICATION NO. : 10/376099
DATED : April 4, 2006
INVENTOR(S) : Hamada et al.

It is certified that error appears in the above-identified patent and that said Letters Patent is hereby corrected as shown below:

Column 13
Lines 4 to 24, replace the chemical structure diagram labeled "TCTA" with:

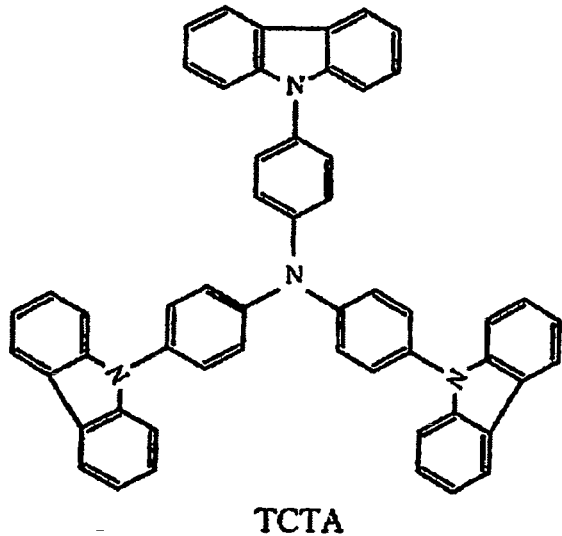

TCTA

Column 18
Line 21, after "may", replace "he" by --be--.

Signed and Sealed this

Twenty-eighth Day of November, 2006

JON W. DUDAS
*Director of the United States Patent and Trademark Office*